United States Patent
Kuth et al.

(10) Patent No.: US 7,609,868 B2
(45) Date of Patent: Oct. 27, 2009

(54) DIAGNOSTIC IMAGING SYSTEM AND METHOD PROVIDING INFORMATION REGARDING BLOOD FLOW IN AN ANATOMICAL ANOMALY

(75) Inventors: Rainer Kuth, Herzogenaurach (DE); Axel Schreiber, Erlangen (DE); Christoph Zindel, Uttenreuth (DE)

(73) Assignee: Siemens Aktiengesellschaft, Munich (DE)

( * ) Notice: Subject to any disclaimer, the term of this patent is extended or adjusted under 35 U.S.C. 154(b) by 738 days.

(21) Appl. No.: 11/348,657

(22) Filed: Feb. 7, 2006

(65) Prior Publication Data

US 2006/0239529 A1    Oct. 26, 2006

(30) Foreign Application Priority Data

Feb. 8, 2005  (DE) ............... 10 2005 005 687

(51) Int. Cl.
*G06K 9/00* (2006.01)
(52) U.S. Cl. .............................. 382/128
(58) Field of Classification Search ......... 382/128–134; 128/920–930; 250/455–465; 356/39–49
See application file for complete search history.

(56) References Cited

U.S. PATENT DOCUMENTS

| | | | |
|---|---|---|---|
| 6,549,798 B2 * | 4/2003 | Stefancik et al. ............ | 600/419 |
| 2001/0031920 A1 * | 10/2001 | Kaufman et al. ............ | 600/431 |
| 2003/0114759 A1 * | 6/2003 | Skyba et al. ................ | 600/458 |
| 2003/0220563 A1 * | 11/2003 | Schutt ........................ | 600/431 |
| 2004/0044281 A1 * | 3/2004 | Jesberger et al. ............ | 600/419 |
| 2004/0147835 A1 | 7/2004 | Kiefer et al. | |
| 2006/0122492 A1 * | 6/2006 | Kucharczyk et al. ........ | 600/420 |

FOREIGN PATENT DOCUMENTS

EP    0 959 363    10/2003

OTHER PUBLICATIONS

A Review of Technical Advances in Virtual Colonoscopy, pp. 938-942, Serile et al, Medinfo 2001.
Interactive Polyp Biopsy Based on Automatic Segmentation of Virtual Colonoscopy, Ko et al, (2004)—Proceedings of the Fourth IEEE Symposium on Bioinformatics and Bioengineering.

* cited by examiner

*Primary Examiner*—Samir A. Ahmed
*Assistant Examiner*—Atiba O Fitzpatrick
(74) *Attorney, Agent, or Firm*—Schiff Hardin LLP

(57) ABSTRACT

An imaging diagnosis system for generation of a three-dimensional image data set of an examination subject has an image acquisition unit that acquires three-dimensional raw data of the examination subject, an image reconstruction unit that generates a three-dimensional image data set from the three-dimensional raw data, an image processing unit that detects anatomical structures of the examination subject from the image data set, and a position determination unit that determines the position of an anomaly (identified by a diagnostician) in the anatomical structures of the examination subject in the image data set and generates position data for the image acquisition unit. The image acquisition unit acquires perfusion-sensitive raw data with the aid of the position data of the detected anomaly, which perfusion-sensitive raw data contain perfusion information of the identified anomaly.

11 Claims, 4 Drawing Sheets

DIAGNOSTIC IMAGING SYSTEM AND METHOD PROVIDING INFORMATION REGARDING BLOOD FLOW IN AN ANATOMICAL ANOMALY

BACKGROUND OF THE INVENTION

1. Field of the Invention

The present invention concerns a diagnostic imaging system for generation of a three-dimensional image data set of an examination subject as well as a method for determination of information about the perfusion of an anatomical anomaly in an examination subject. The invention is particularly suitable for use in the treatment of intraluminal pathologies of the gastrointestinal tract and in particular can be used before the removal of polyps in the intestine of a patient to obtain information about the vascular supply (vasculature) of the polyps.

2. Description of the Prior Art

Polyps in the region of the large intestine are a common disorder. These are initially benign but can grow over several years (on average between 5 to 8 years) and, with a very high probability, develop into malignant tumors (known as the adenoma-carcinoma sequence) over time. The larger the polyp, the greater the probability of its degeneration. Given early treatment, the polyp can be removed with a curative approach (thus in a benign state). Polyps normally are removed in a minimally-invasive manner by means of flexible endoscopy and with thermal removal (ablation) methods. For example, the polyps can be severed at an optimal depth by means of a small cutting tool (loop). The bleeding that arises should be stopped by coagulation. During their growth phase, polyps can form quite large venous and/or arterial vessels that are normally not externally visible to the treating endoscopy physician. After the severing of the polyps, blood flows from the severed vessels. Given a diameter of more than 5 mm and in particular in the case of patients with high blood pressure and/or patients who take blood-thinning medication, the bleeding is not stanched by blood clotting at the cutting site. In many cases, the coagulation (for example due to an RF current with an RF loop) is not sufficient. In the short term such bleeding can require a surgical operation with a transection of the hypogastric region. Other than by the use of a double catheter, which can be used only with difficulty via the working channel of an endoscope, the endoscopic physician has no possibility to determine the vascular status of the polyps beforehand (before the severing of the polyps) and to establish whether the severing will have a small, medium or even a high risk. If bleeding occurs upon severing, this is often sudden and requires a quick procedure (intervention).

DE 102 52 852 A1 describes a processing device of a magnetic resonance system that allows a graphical measurement (data acquisition) using already-acquired, corrected MR overview images, wherein the region of the corrected MR overview image is graphically delimited by other regions.

Furthermore, by means of acquired image data sets from imaging systems such as MR or CT systems, the examined regions can be represented virtually post-processing a three-dimensional image data set in order, for example, to represent the anatomy by segmentation of the images. A virtual colonoscopy (large intestine endoscopy) is likewise possible with the acquired three-dimensional image data sets, in which the intestine can be virtually "flown through" and the intestinal walls can be examined for possible pathologies. Such a virtual colonoscopy is described, for example, in "A review of technical advances in virtual colonoscopy" in Medinfo 2001, Netherlands, Vol. 10, Nr. 3, p. 73-79.

EP 0 959 363 B1 describes magnetic resonance arteriography with dynamic intravenous contrast agent injection.

An automatic segmentation of the colon wall is described in "Interactive polyp biopsy based on automatic segmentation of virtual colonoscopy" in BIBE 2004, Proceedings, Fourth IEEE Symposium on Bioinformatics and Bioengineering, 19-21 May 2004, p. 159-166.

Among other things, it is currently a goal to detect as early as possible the existing risks upon removal of a polyp with regard to the bleeding behavior. It can then be decided from the outset which patients can be treated by means of an operation and which by flexible endoscopy.

For this purpose it is desirable to obtain information about the vascularization of the region to be several before the removal of a pathology. Miniaturized Doppler ultrasound endoscopic probes are available, but their use is too complicated to be routine. Among other things, it is known to insert a piezo-probe into the patient via an endoscope, in an attempt to conclude the vascularization of the polyps to be removed from the flow noise in their proximity. This is, however, difficult and error-prone.

SUMMARY OF THE INVENTION

An object of the present invention is to provide a simple way to obtain information about the perfusion of an anomaly to be removed of an anatomical structure.

This object is inventively achieved by a diagnostic imaging system and a method according to the invention, the diagnostic imaging system for generation of a three-dimensional image data set of an examination subject including an image acquisition unit that acquires three-dimensional raw data from the examination subject. Furthermore, an image reconstruction unit is provided that generates a three-dimensional image data set from the three-dimensional raw data. An image processing unit detects anatomical structures of the examination subject by post-processing from the image data set. Furthermore, the position determination unit is provided that determines a position of an anomaly (identified by a diagnostician) of the anatomical structure in the image data set and furthermore generates position data for the image acquisition unit. Furthermore, with the aid of the position data the image acquisition unit acquires perfusion-sensitive raw data (and/or angiographic data that contain perfusion information and/or information about the vascularization of the identified anomaly) from the detected anomaly. With the inventive diagnostic imaging system it is possible to non-invasively classify the blood supply and/or vascularization of an anatomical anomaly, such that before the removal of the anomaly it can be established in which manner the anomaly should be removed, such as by micro-invasive methods such as endoscopy or by a conventional operation. The image processing unit can virtually represent the acquired anatomical structure, so that anomalies or pathological tissue can also be recognized and detected. The position of the anomaly to be removed is thus known in the image data set. Position data of the detected anomaly are generated from this for the diagnostic imaging system, in particular for the image acquisition unit. Local perfusion-sensitive and/or angiographic images of the anomaly, that can subsequently be evaluated, are generated with the image acquisition unit. As usual herein, the term "three-dimensional image data" means that either a number of slices (2D) are acquired that are merged (multi-slice technique), or that a 3D data volume is acquired instead of the multi-slice technique.

In a preferred embodiment, the evaluation unit generates information about the perfusion of the anomaly from the perfusion-sensitive raw data.

For the position determination of the anomaly, the position determination unit can advantageously determine the position data (X1, Y1, Z1) of the anatomical anomaly in a coordinate system (X, Y, Z) in the image data set. The position determination unit subsequently generates position data (u1, v1, w1) for the image acquisition unit, or which describe the position of the anomaly in a coordinate system (u, v, w), this is done by applying an inverse transformation matrix to the position data (X1, Y1, Z1). For generation of the image data, the transformation matrix of which the inverse transformation matrix is an inverse is used to transfer the position data of the examined subject into the coordinate system (u, v, w) of the image acquisition unit by the application of this transformation matrix in the image data set. The inverse transformation matrix is then used to transfer the position data in the coordinate system (X, Y, Z) of the image data set into position data in the coordinate system (u, v, w) of the image acquisition unit.

The evaluation unit can generate information about the perfusion of the acquired anomaly, with at least one of the following items of information being generated: local blood volume of the anomaly, local blood flow through the anomaly, local average transit time through the anomaly, local vessel permeability of the anomaly.

Furthermore, the evaluation unit can be fashioned such that the existence of vessels in the anomaly is examined at a diameter greater than 1, 2 or 5 mm. The above criteria help the treating doctor in the establishment of whether the anomaly can be removed in a minimally-invasive manner with a catheter, or whether the danger of bleeding upon severing of the anomaly is so large that an operation on the patient is necessary.

In a preferred embodiment, exposures of the gastrointestinal tract are acquired by the image acquisition unit in order to visualize a pathology of the lumen of the gastrointestinal tract; whereby in particular exposures of the large intestine are generated. The image processing unit detects the intestine by segmentation, so the diagnostician can detect polyps in the intestinal wall as anomalies. As already mentioned, polyps in the region of the large intestine are a frequently-occurring disorder (particularly in the civilized, industrial nations), and these polyps frequently develop into malignant tumors. By using the three-dimensional image data set of the intestine, a virtual colonoscopy is possible, so polyps in the intestinal wall can be upon viewing of the virtual colonoscopy on the screen of a computer unit.

It is requirement for this purpose that the spatial resolution of the imaging system be so good that polyps can be detected in a size range of, for example, 1 cm. The diagnostic imaging system is preferably a magnetic resonance system that generates image data sets of the examination subject by nuclear magnetic resonance, in which case the image acquisition unit uses perfusion-sensitive T1-weighted or T2*-weighted imaging sequences. Magnetic resonance systems (MR tomography system) and the images therefrom provide a good soft tissue contrast, and the spatial resolution is good enough that possible polyps can be shown well in a spatial sense.

The present invention, however, is naturally not limited to imaging MR magnetic resonance systems. It is likewise possible to use a computed tomography system (CT) as the diagnostic imaging system.

A contrast agent that is injected into the examination subject preferably is used for the generation of the perfusion-sensitive or angiographic raw data of the examined anomaly or of the examined polyp. The contrast agent can be administered, for example, as a bolus, with the passage (flow) of the contrast agent bolus through the polyp or polyps being detected with high-resolution temporal measurements. The temporal resolution is selected such that the acquisition time of an image is under two seconds (preferably under one second) in order to be able to well-represent the contrast agent progress. Among other things, fast gradient echo sequences can be used as imaging-sequences in magnetic resonance tomography, particularly for examinations in the abdominal area. Naturally, other imaging sequences are also possible that enable the contrast agent progress to be represented.

The evaluation unit preferably compares the perfusion information or angiography information of the anatomical anomaly (such as the polyp) with perfusion information or angiography information of tissues that are morphologically without pathological findings such as, for example, morphologically non-pathological mucous membrane. From this comparison, conclusions about the vascular supply of the polyps can be made with regard to the cross-section of the vascular base, its flow resistance, and the permeability of the vessel wall.

The evaluation unit preferably superimposes the perfusion information of the anomaly on the anatomical images of the anomaly. With these superimposition images, the doctor sees an indication of the presence of a large vessel in the polyp that supplies the polyp, such that the removal of these polyps can be planned taking this information into consideration.

The present invention likewise concerns a method for determination of information about the perfusion of an anatomical anomaly in an examination subject with the following steps:

Three-dimensional raw data of the examination subject are initially acquired. A three-dimensional image data set is subsequently reconstructed from the raw data. Furthermore, the anatomical structure of the examination subject is shown via post-processing of the image data set. When an anatomical anomaly is detected (i.e. is visually identified) given viewing of the image data set by the doctor, the position of the detected anomaly is determined in the image data set. Furthermore, position data are generated for an diagnostic imaging system. A perfusion-sensitive or angiographic measurement sequence is acquired with the aid of these position data, i.e. perfusion-sensitive raw data of the anomaly are acquired. The perfusion information is subsequently extracted from the raw data. With the inventive method, after review of the image data set and the detection of an anomaly it is possible to automatically generate perfusion-sensitive image data of this anomaly and to extract the perfusion information.

As previously mentioned, a possible region for examination is the gastrointestinal tract, such that the gastrointestinal tract is exposed and a three-dimensional image data set of this is generated, whereby pathologies of the lumen should be detected as anatomical anomalies. As mentioned, the intestine is preferably examined, with the examination serving to detect polyps in the intestinal wall.

When the raw data can be acquired by means of nuclear magnetic resonance, MR angiographies (such as contrast agent-supported angiographies, time-of-flight angiographies or phase contrast angiographies) can also be used in addition to T1-weighted or T2*-weighted imaging sequences. MT angiographic techniques are known in the art and need not be explained in detail herein.

The flow speed in the anomaly or in a polyp and/or the average transit time of a contrast agent that is injected during the examination preferably is measured, whereby the average transit time of the contrast agent through the anomaly is calculated.

From the perfusion measurements, conclusions about the vascular supply of a polyp can subsequently be made with regard to the cross-section of the vascular bed, the flow resistance of the polyps, and about the permeability of the vessel wall of the polyps. In the method it is in particular examined whether vessels with a diameter greater than 2 mm, particularly greater than 5 mm, are present in the polyps to be removed.

DESCRIPTION OF THE PREFERRED EMBODIMENTS

Figure 1:
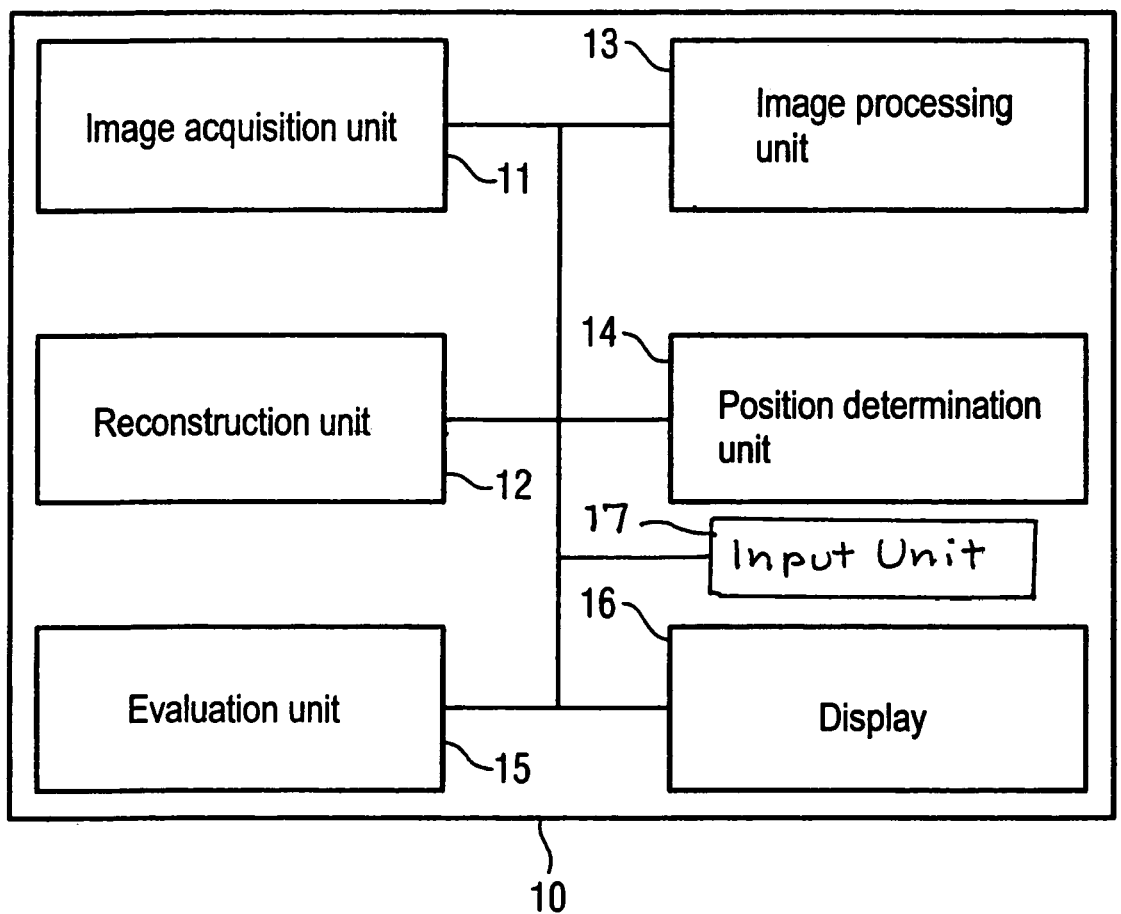
FIG. 1 schematically illustrates a diagnosis system which provides perfusion information of an examination subject.

FIG. 1 schematically shows an diagnostic imaging system 10, which is an important component for the planning of a removal of a polyp. The diagnostic imaging system 10 has an image acquisition unit 11 that acquires images of an examination subject (not shown). The image acquisition unit, for example, can be an MR tomograph or a CT tomography apparatus. The image acquisition unit 11 acquires three-dimensional raw data of a patient, and a reconstruction unit 12 generates a three-dimensional image data set of the examination subject. This image data set is subsequently further processed by an image processing unit 13. For example, the anatomy contained in the image data set can be shown by segmentation of other image processing techniques. In the case of imaging of the intestine, for example, the intestine or the intestinal wall can be shown, such that via the image processing unit 13 a virtual colonoscopy is possible in which the region of the intestine can be "flown through". If the treating doctor discovers an anomaly in the virtual colonoscopy in the form of a polyp, he or she can mark this on a display 16 via an input unit 17 (such as a mouse). As is explained below in connection with FIG. 3, a position of the polyp in the coordinate system of the diagnosis system is determined by a position determination unit 14 from the position of the polyp in the image data set that corresponds to the position of the polyp marked on the screen of the display 16. When the position of the found polyp is known in the coordinate system of the diagnosis system or of the image acquisition unit 11, the image acquisition unit 11 can implement a perfusion-sensitive imaging sequence for the detected polyp in order to obtain information about its vascularization. An evaluation unit 15 then evaluates the perfusion measurements of the examined polyp and displays the result of the evaluation on the display 16. For example, the results of the perfusion evaluation can be shown in superimposition images together with the anatomy. In the further virtual colonoscopy, the doctor can then detect which of the possibly-present polyps can or must be removed in a minimally-invasive manner and which of the present polyps can or must be removed by an operation, given the presence of large vessels in the polyps. The diagnosis system thus supports the doctor in the decision about the further surgical procedure.

Figure 2:
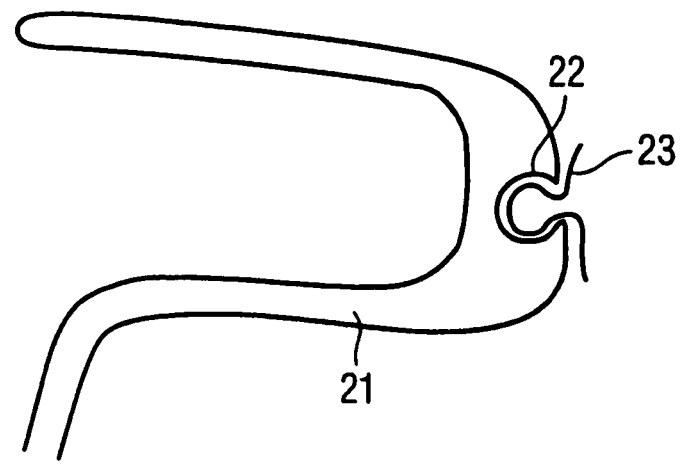
FIG. 2 schematically shows the presence of a polyp in the wall of the large intestine.

For example, an application field of the invention is shown in FIG. 2, whereby FIG. 2 shows the typical shape of a large intestine. The shown polyp 22 can have a size, for example, of 2 cm. In the shown case, a large blood vessel 23 runs through the polyp. If the shown polyp 22 is endoscopically severed, the severed vessel stump would lead to an unstanchable bleeding. The stanching of the bleeding could ensue, for example, by radio-frequency coagulation or endoscopically by clipping of the vessel. However, all of these methods are technically difficult and require of the endoscopic physician a high degree of experience, and likewise exhibit potential complications. The vascularization of the polyp 22 can be automatically detected in a non-invasive manner with the diagnosis system shown in FIG. 1.

Figure 3:
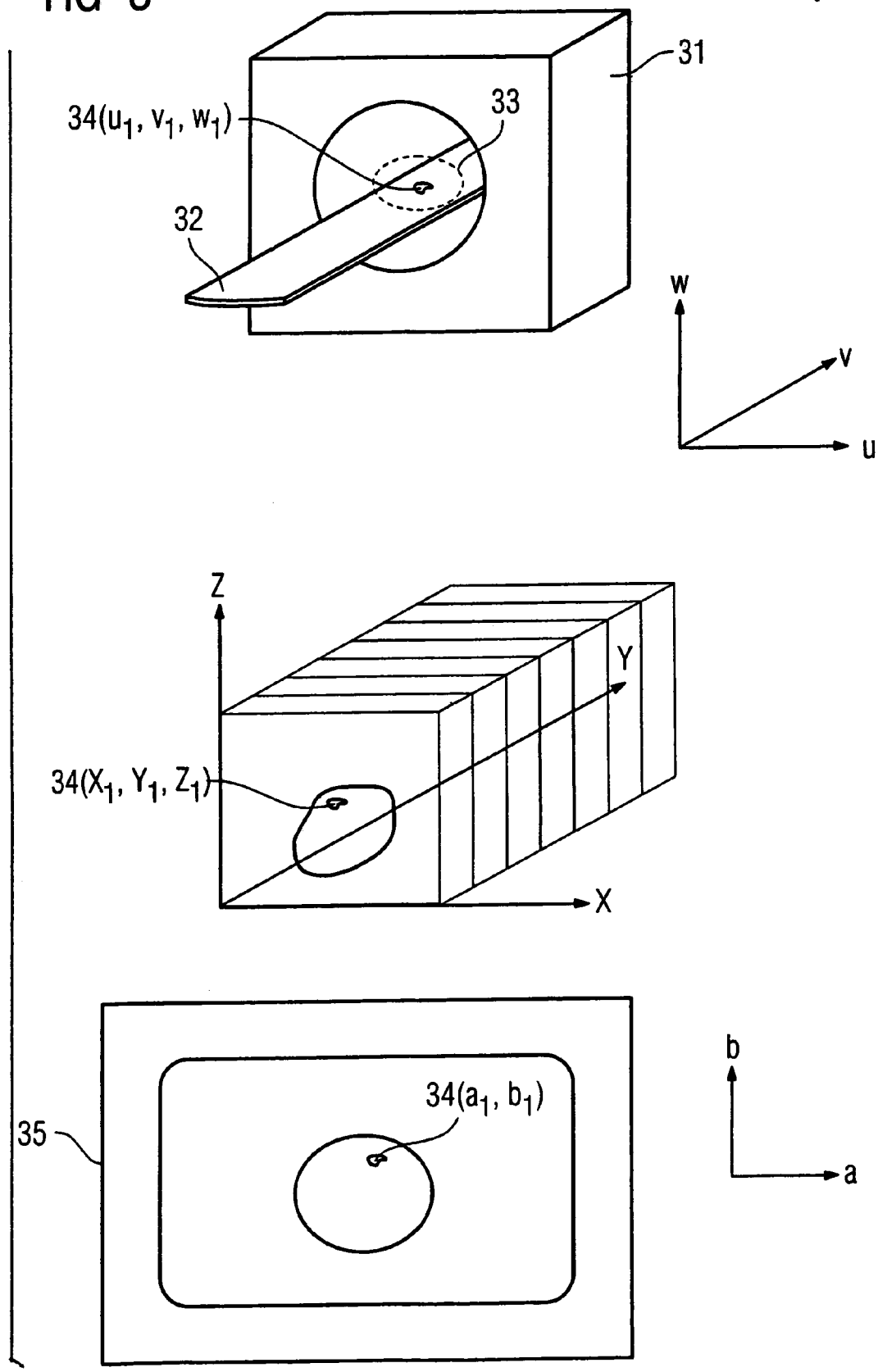
FIG. 3 illustrates the various coordinate systems of the system in order to generate position data for the diagnostic imaging system.

In FIG. 3 it is shown how position coordinates are determined for the imaging system in the coordinate system of the screen after detection of an anomaly such as a polyp on the screen, so that the imaging system can implement spatially delimited perfusion acquisitions. At the top of FIG. 3, an diagnostic imaging system in the form of an MR apparatus 31 is schematically shown. A part of the patient (examination subject) 33 is schematically shown on a patient bed 32. The patient 33 has a polyp 34 at the position (u1, v1, w1) in the coordinate system (u, v, w) of the MR apparatus 31. In the image acquisition, a raw data set for the virtual colonoscopy is acquired by the MR apparatus 31 and is shown in an image data set. This three-dimensional image data set in the coordinate system (X, Y, Z) of the image data also contains the polyp 34 in the patient 33. This polyp 34 has the coordinates (X1, Y1, Z1) in the image data set. The image data set of the coordinate system (X, Y, Z) is used for generation of the virtual colonoscopy, with which the doctor is able to observe the inner intestinal wall along its length and to examine it for possible polyps. The image post-processing possibilities used given the use for generation of such virtual techniques in order to detect the walls of the examination subject are known to the person of ordinary skill in the art, for example by via segmentation of the image data set.

The three-dimensional shape of the anatomy is two-dimensionally shown on the screen 35 in a coordinate system (a, b). Given "fly-through" through the anatomy or, respectively, through the intestine of the patient 33, the doctor detects (for example) the polyp 34 and marks the point of the polyp with the coordinates (a1, b1). From the marked position (a1, b1) on the screen, the position determination unit 14 calculates the position (X1, Y1, Z1) of the polyp 34 in the coordinate system (X, Y, Z) of the image data. So that the MR apparatus can make a perfusion-sensitive local exposure of the polyp 34, the precise localization of the polyp (u1, v1, w1) in the coordinate system of the MR apparatus (u, v, w) must be known. For this purpose, it is necessary to transform the coordinates (X1, Y1, Z1) of a polyp 34 found in the virtual colonoscopy back into the coordinate system (u, v, w) of the MR apparatus 31, for which purpose an inverse transformation matrix is applied. For the generation of the image data set in the coordinate system (X, Y, Z), the coordinates (u, v, w) of the polyp 34 in the MR apparatus 31 are transformed into coordinates (X, Y, Z), by the application of the matrix of which the aforementioned inverse transformation matrix is an inverse. After discovery of a polyp, this method must be reversed such that, to determine the position of the polyp, these must be determined in the coordinate system of the diagnostic imaging system by application of the inverse transformation matrix.

Figure 4:
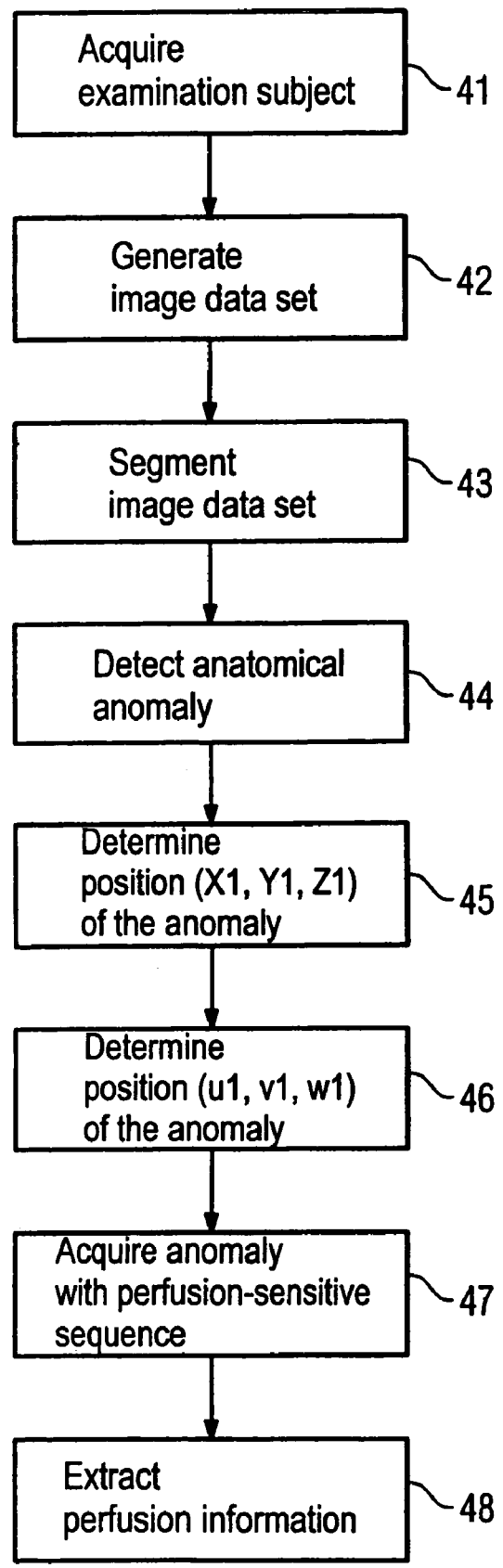
FIG. 4 is a flow diagram that schematically shows a method with which information about the perfusion of an anomaly are automatically available.

The various steps are shown in FIG. 4 that, by obtaining perfusion information, represent a component for the planning of a removal of an anatomical anomaly. The examination subject is exposed in a step 41. In a step 42, an image data set is subsequently generated by the image reconstruction unit from FIG. 1. This image data set is subsequently segmented in a step 43 by known image post-processing techniques in order to show the anatomical structures of boundary surfaces of the anatomical structures. When an anatomical anomaly is detected in the next step 44, the position data of the anomaly (X1, Y1, Z1) must be determined in the coordinate system (X, Y, Z) of the image data set. So that a conclusion about the perfusion or vascular supply of the detected anomaly is possible, an imaging of the detected anomaly must be implemented locally. For this, in a step 46 the position of the anomaly must be determined for the coordinate system of the diagnosis system (u, v, w). According to the invention, this can ensue automatically via the position determination unit 14 after the doctor has marked the position of the anomaly with the position data (a1, b1) from FIG. 3. Only when the position of the anomaly is established can a perfusion-sensitive or angiographic imaging sequence of the anomaly be acquired in step 47. In the sequence, contrast agent can additionally be worked with in order to obtain information about the local blood volume, the local blood flow, the local average transit time, the local vessel permeability, and the point in time at which the maximal concentration of the contrast agent in the tissue is reached.

The perfusion information is then extracted and optionally displayed in a step 48.

Figure 5:
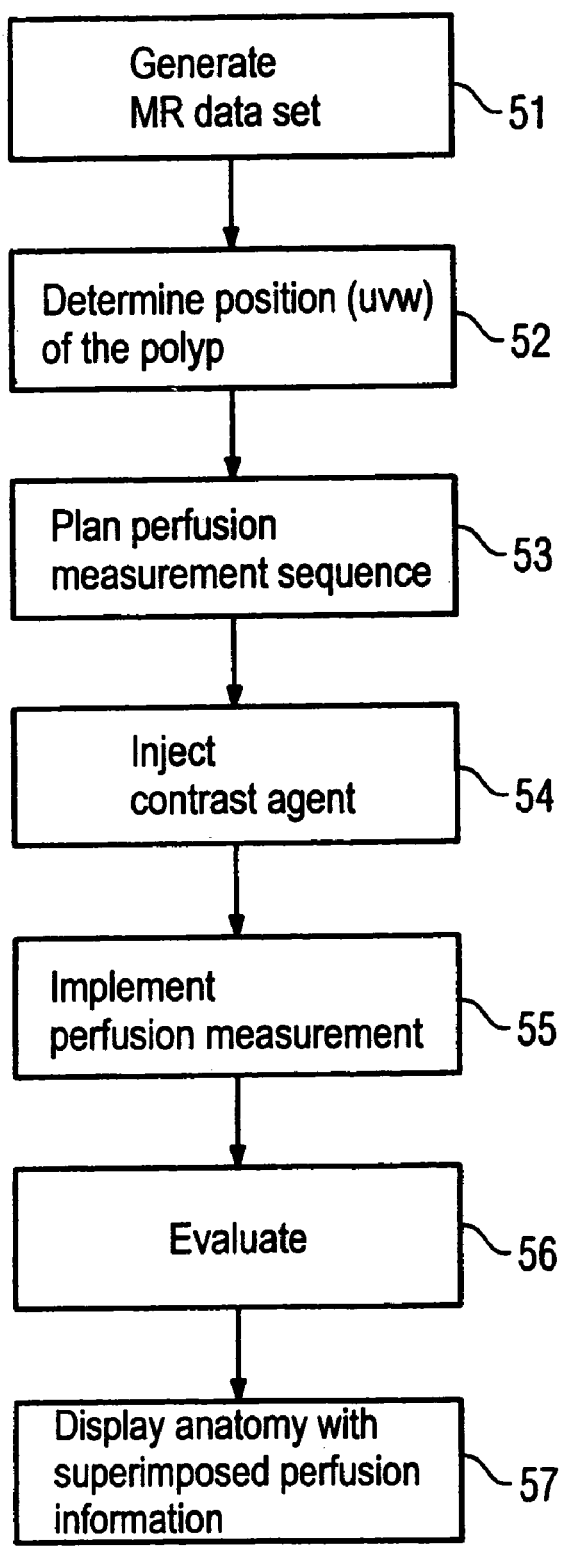
FIG. 5 is a flow diagram of a further method for generation of perfusion data of a polyp.

The various steps when a magnetic resonance system is used as an diagnostic imaging system are shown in FIG. 5. In a first step 51, a three-dimensional MR data set is generated, whereby the gastrointestinal tract is exposed with a suitable MR imaging sequence. As in FIG. 4, a three-dimensional image data set is subsequently generated in the steps 42 through 44 for the virtual colonoscopy, in which three-dimensional image data set the doctor can then mark the coordinates (a1, b1) of the polyp using the screen representation in order to then determine the position (u1, v1, w1) of the polyp via the cords (X1, Y1, Z1) in the coordinate system (X, Y, Z) of the image data set. The image acquisition unit 11 can subsequently plan a perfusion measurement sequence or angiography sequence and its spatial-association (step 53). In the case of the examination of the intestine, the perfusion measurement sequence can, for example, be a fast two-dimensional gradient echo sequence that is situated such that it runs through the polyp. However, other fast imaging sequences are also possible that are in the position to generate images of the polyp in the intestinal wall at a temporal resolution of 1 to 2 seconds. Theoretically, an echo planar imaging is also possible, however this would be difficult to apply given the application in the abdominal area due to the air present and the susceptibility transitions [transfers] connected with this. However, in principle any imaging sequence is possible that can show information about the perfusion with a high temporal resolution. The measurement sequence with high temporal resolution is necessary since a contrast agent is injected into the patient (step 54) to obtain the perfusion information. The perfusion measurement is implemented in a step 55 during the contrast agent injection, whereby MR angiography techniques can also be used for representation of the vessel course in the polyp. The perfusion measurement is subsequently evaluated in a step 56, whereby in the case of an angiography the vascular supply of the intestine and, if applicable, the larger vessels that supply the polyp are shown. The perfusion measurement is evaluated with regard to the local blood volume, the local blood flow, the local average transit time, the local vessel permeability and the point in time at which the maximal concentration of the contrast agent in the tissue is reached. Conclusions can be made from these about the vascular supply of the polyp with regard to the cross-section of the vascular bed, its flow resistance, and the permeability of the vessel wall. The found information can subsequently be shown in a superimposition image together with the anatomy in the three-dimensional data set, such that the treating doctor receives reliable information as to how the found polyp must be removed.

The present invention improves the planning of a removal of an anatomically anomaly. The classification of the vascularization of a polyp is thereby enabled.

Although modifications and changes may be suggested by those skilled in the art, it is the intention of the inventors to embody within the patent warranted hereon all changes and modifications as reasonably and properly come within the scope of their contribution to the art.

We claim as our invention:

1. A diagnostic imaging system comprising:
an image acquisition unit adapted to interact with an examination subject to acquire three-dimensional raw image data from the examination subject;
an image reconstruction unit connected to said image acquisition unit that generates a three-dimensional image dataset from said three-dimensional raw image data; and
a position determination unit and an input unit connected thereto, said input unit allowing a user to designate, in said three-dimensional image dataset, an anatomical anomaly in said examination subject, and said position determination unit, from said designation, generating position data supplied to said image acquisition unit to cause said image acquisition unit to acquire further data, selected from the group consisting of perfusion-sensitive data and angiographic raw data, from the examination subject at a location dependent on said position data, said further data containing information indicative of blood flow in said anatomical anomaly.

2. A diagnostic imaging system as claimed in claim 1 wherein said image acquisition unit has an image acquisition unit coordinate system associated therewith and wherein said image dataset comprises image data having an image data coordinate system associated therewith, and wherein said position data have a position data coordinate system associated therewith, and wherein said position determination unit determines said position data in said image dataset in said image data coordinate system by applying an inverse of a transformation matrix to said position data and wherein said image reconstruction unit generates image data representing said anatomical anomaly by applying said transformation matrix to said position data.

3. A diagnostic imaging system as claimed in claim 1 comprising an evaluation unit supplied with said further data, said evaluation unit generating a characteristic of blood flow in said anatomical anomaly from said further data, as said information indicative of blood flow in said anatomical anomaly.

4. A diagnostic imaging system as claimed in claim 3 wherein said evaluation unit generates said characteristic from the group consisting of local blood volume in said anatomical anomaly, local blood flow through said anatomical anomaly, local average transit time of blood through said anatomical anomaly, local vessel permeability of said anatomical anomaly, and existence of vessels in said anatomical anomaly having a diameter greater than 5 mm.

5. A diagnostic imaging system as claimed in claim 1 wherein said image acquisition unit acquires said three-dimensional raw data of the intestinal tract of said examination subject as a plurality of exposures, and comprising an image processing unit that detects the intestinal tract by segmentation, and wherein said anatomical anomaly is a polyp in the intestinal wall in said intestinal tract.

6. A diagnostic imaging system as claimed in claim 1 wherein said image acquisition unit is a magnetic resonance scanner, and wherein said magnetic resonance scanner acquires said further data by implementing an imaging sequence selected from the group consisting of perfusion-sensitive T1-weighted imaging sequences and perfusion-sensitive T2*-weighted imaging sequences.

7. A diagnostic imaging system as claimed in claim 1 wherein said image acquisition unit is a computed tomography scanner.

8. A diagnostic imaging system as claimed in claim 1 comprising a contrast agent injector adapted to interact with the examination subject during acquisition of said further data, to inject contrast agent into the examination subject.

9. A diagnostic imaging system as claimed in claim 1 comprising an evaluation unit supplied with information indicative of said blood flow in said anatomical anomaly that compares said information indicative of blood flow information of said anatomical anomaly with comparable blood flow information of comparable non-pathological tissue.

10. A diagnostic imaging system as claimed in claim 1 comprising an evaluation unit that superimposes said information indicative of blood flow in said anatomical anomaly on a displayed anatomical image of said anatomical anomaly.

11. A diagnostic imaging system as claimed in claim 1 comprising an image processing unit that detects anatomical structures of said examination subject from said image dataset.

* * * * *